United States Patent [19]
Theissen

[11] 4,367,090
[45] Jan. 4, 1983

[54] HERBICIDAL N-(5,5-DIMETHYLOXAZOLIDENEYL-2,4-DIONE) 5-(SUBSTITUTED PHENOXY-2-SUBSTITUTED BENZAMIDES

[75] Inventor: Robert J. Theissen, Bridgewater, N.J.

[73] Assignee: Rhone-Poulenc Agrochimie, Lyon, France

[21] Appl. No.: 284,310

[22] Filed: Jul. 17, 1981

[51] Int. Cl.³ .................... C07D 263/32; A01N 43/76
[52] U.S. Cl. ........................................ 71/88; 548/226; 546/275; 71/94
[58] Field of Search ............................ 548/226; 71/88

[56] References Cited

U.S. PATENT DOCUMENTS

| | | | |
|---|---|---|---|
| 3,784,635 | 1/1974 | Theissen | 260/471 R |
| 4,002,662 | 1/1977 | Theissen | 71/105 |
| 4,093,446 | 6/1978 | Bayer et al. | 71/88 |
| 4,173,464 | 11/1979 | Noguchi et al. | 71/88 |
| 4,209,318 | 6/1980 | Johnson | 71/88 |
| 4,227,914 | 10/1980 | Föry et al. | 71/88 |

Primary Examiner—Donald G. Daus
Assistant Examiner—Sharon A. Gibson
Attorney, Agent, or Firm—Morgan, Finnegan, Pine, Foley & Lee

[57] ABSTRACT

There are provided herbicidal N-(5,5-dimethyloxazolideneyl-2,4-dione) 5-(substituted phenoxy or pyridyloxy)-2-substituted benzamides.

5 Claims, No Drawings

HERBICIDAL N-(5,5-DIMETHYLOXAZOLIDENEYL-2,4-DIONE) 5-(SUBSTITUTED PHENOXY-2-SUBSTITUTED BENZAMIDES

BACKGROUND OF THE INVENTION

Herbicidal 5-[2-chloro-4-(trifluoromethyl)phenoxy]-2-nitrobenzoic acid and salts thereof, and various herbicidal derivatives of these compounds have been proposed including alkyl and cycloalkyl esters, alkylthio esters, phenyl ester, alkyl and dialkyl amido and benzoyl chloride forms. U.S. Pat. which describe such compounds and the like include Nos. 3,652,645; 3,784,635; 3,873,302; 3,983,168; 3,907,866; 3,798,276; 3,928,416; and 4,063,929.

SUMMARY OF THE INVENTION

This invention provides certain herbicidal compounds of the formula:

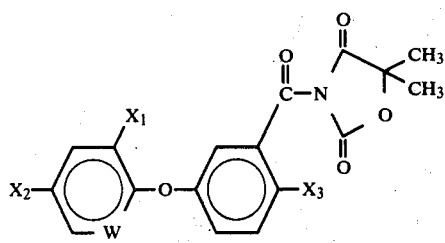

where:

(i) W is C-$X_4$ or N; and (ii) $X_1$, $X_2$, $X_3$ and $X_4$ are groups which are capable of being incorporated into Formula I and which collectively impart herbicidal activity thereto.

Preferably, $X_4$ is halogen (e.g., F, Br or, especially, Cl) or, especially, H. Examples of the groups $X_1$, $X_2$ and $X_3$ include halogen (e.g., F, Cl and Br), polyhaloalkyl (e.g., $C_1$-$C_4$ alkyl with from 2-9 halogens such as, especially, $CF_3$), $NO_2$, CN, alkyl (e.g., $C_1$-$C_4$ alkyl), $SO_2$ alkyl (e.g., having 1-4 carbon atoms), $SO_2NH_2$, NO, COO alkyl (e.g., having 2-5 carbon atoms) and COOH.

A preferred form of Formula I is of the formula:

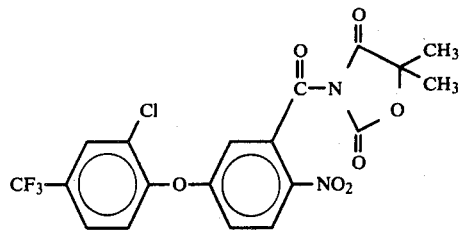

The following compounds as defined by formula I were prepared:

| Compound No. | Structure | MP. °C. |
|---|---|---|
| 1 | ![structure 1] | 129-32 |
| 2 | ![structure 2] | 144-8 |
| 3 | ![structure 3] | oil |

EXAMPLE

Preparation of N-(5,5-dimethyloxazolideneyl-2,4-dione) 5-[2-chloro-4-trifluoromethyl)phenoxy]-2-nitrobenzamide.

To a stirred solution of 5-[2-chloro-4-trifluoromethyl)phenoxy]-2-nitrobenzoyl chloride (6.7 g, 0.02 mole) in ether (100 ml) was added triethylamine (2.1 g., 0.02 mole) in ether (5 ml) and solid 5,5-dimethyloxazolideneyl-2,4-dione. An immediate heavy precipitate formed and the temperature rose to 30° C. The reaction was refluxed overnight. The cooled solution was filtered and the precipitate washed several times with small portions of acetone. The combined ether-acetone filtrate was concentrated to give 9.2 g. of a white solid, m.p. 122°-7°.

Recrystallization from toluene-hexane gave 6.7 g., m.p. 129°-32° C.

I.R. (nujol): C=o 1850 (weak), 1790 (strong) and 1735 (weak) cm$^{-1}$

NMR[(CD$_3$)$_2$CO]: singlet 1.60 ppm (6H) complex multiplet 7.0-8.5 (6H)

The compounds of Formula I may yield open chain analogs of the following formula when reacted with nucleophiles —QR, e.g., O alkyl, S alkyl, N (alkyl)$_2$

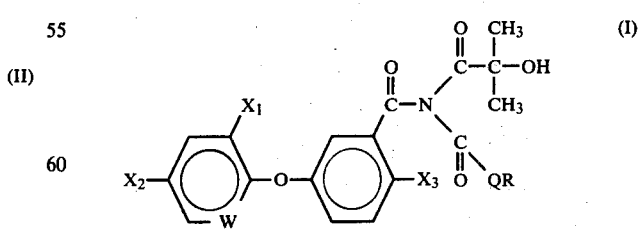

The compounds of this invention can be applied in various ways to achieve herbicidal action. They can be applied per se, but may be applied as the toxic components in pesticidal compositions of the compound and a carrier. These compositions may be applied directly to the soil and often incorporated therewith. The compositions can be applied as granulars or dusts; as liquid sprays, or as gas-propelled sprays and can contain, in addition to a carrier, additives such as emulsifying agents, binding agents, gases compressed to the liquid state, odorants, stabilizers, and the like. A wide variety of liquid and solid carriers can be used. Non-limiting examples of solid carriers include talc, bentonite, diatomaceous earth, pyrophyllite, fullers earth, gypsum, flours derived from cotton seeds and nut shells, and various natural and synthetic clays having a pH not exceeding about 9.5. Non-limiting examples of liquid carriers include water, organic solvents such as alcohols, ketones, light oils, and medium oils and vegetable oils such as cottonseed oil. In practice, herbicidal application is measured in terms of pounds of herbicide applied per acre. The compounds of this invention are effective herbicides when applied in herbicidal amounts, e.g., at rates between about 0.03 pound and about 10 pounds per acre.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A herbicidal compound of the formula

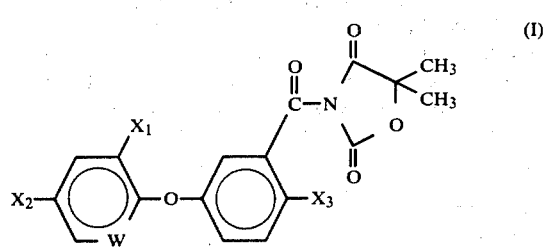

(I)

where:
(i) W is C-$X_4$; and
(ii) $X_1$, $X_2$, $X_3$ and $X_4$ are groups which are capable of being incorporated into Formula I and which collectively impart herbicidal activity thereto.

2. A compound according to claim 1 wherein:
(i) $X_4$ is H or halogen; and
(ii) $X_1$, $X_2$ and $X_3$ are selected from the group consisting of halogen, polyhaloalkyl, $NO_2$, CN, alkyl, $SO_2$ alkyl, $SO_2NH_2$, NO, COO alkyl and COOH.

3. A compound according to claim 2 selected from the group consisting of

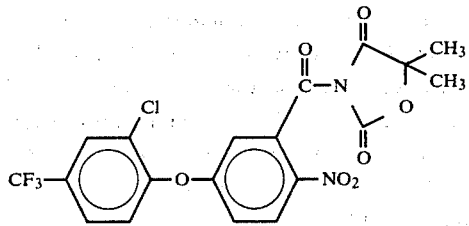

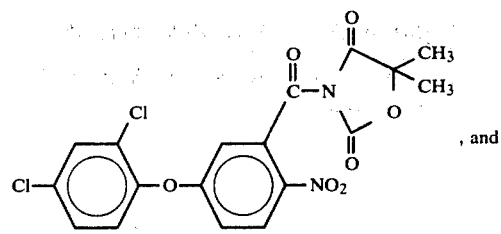

, and

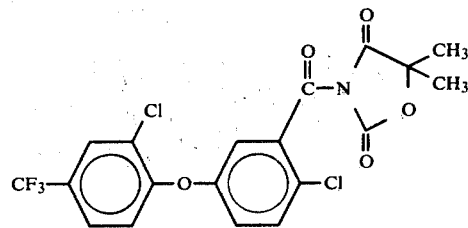

4. A herbicidal composition comprising a compound according to any one of claims 1 to 3 and an agronomically acceptable carrier.

5. A method for combating unwanted plants which comprises contacting them with a herbicidally effective amount of a compound according to any one of claims 1 to 3.

* * * * *